US011783923B2

(12) United States Patent
Kuchibotla et al.

(10) Patent No.: US 11,783,923 B2
(45) Date of Patent: Oct. 10, 2023

(54) SYSTEMS AND METHODS FOR TRACKING PATIENT EVENTS

(71) Applicant: Flatiron Health, Inc., New York, NY (US)

(72) Inventors: Anand Kuchibotla, New York, NY (US); Dominic Green, New York, NY (US); Eitan Meir Konigsburg, South Orange, NJ (US); Janet Donegan, Park City, UT (US); Jessie Tseng, Brooklyn, NY (US); Lauren Sutton, New York, NY (US); Rahul Bafna, New York, NY (US); Raman Choudhry, New York, NY (US); Angel Leung, Brooklyn, NY (US); Paul Greenleaf, New York, NY (US); Victor J. Wang, New York, NY (US)

(73) Assignee: Flatiron Health, Inc., New York, NY (US)

( * ) Notice: Subject to any disclaimer, the term of this patent is extended or adjusted under 35 U.S.C. 154(b) by 706 days.

(21) Appl. No.: 16/703,346

(22) Filed: Dec. 4, 2019

(65) Prior Publication Data

US 2020/0176093 A1     Jun. 4, 2020

Related U.S. Application Data

(60) Provisional application No. 62/850,069, filed on May 20, 2019, provisional application No. 62/845,581, (Continued)

(51) Int. Cl.
*G16H 10/60* (2018.01)
*G06F 16/2457* (2019.01)
(Continued)

(52) U.S. Cl.
CPC .......... *G16H 10/60* (2018.01); *G06F 16/248* (2019.01); *G06F 16/24578* (2019.01);
(Continued)

(58) Field of Classification Search
CPC ........ G16H 10/60; G16H 15/00; G16H 70/40; G06F 16/24578; G06F 16/248; H04L 9/3247
(Continued)

(56) References Cited

U.S. PATENT DOCUMENTS

| 2013/0179187 A1* | 7/2013 | Jackson | G16H 20/10 705/3 |
| 2014/0200914 A1* | 7/2014 | Rut | G16H 10/20 705/2 |
| 2016/0270659 A1* | 9/2016 | Gandhi | G16B 50/30 |

* cited by examiner

*Primary Examiner* — Joy Chng
(74) *Attorney, Agent, or Firm* — FINNEGAN, HENDERSON, FARABOW, GARRETT & DUNNER, LLP

(57) ABSTRACT

A system for tracking adverse events may include at least one processing device programmed to receive a request from a user to record an adverse event experienced by a patient; receive a search term input by the user; identify, in an adverse event database and based on the search term, at least one database record for an adverse event, wherein the at least one database record includes an adverse event type and at least one characteristic; receive, via an input field, a rating of the at least one characteristic for the patient; generate an adverse event record based on the adverse event type and the rating; and store the adverse event record in an adverse event log.

31 Claims, 28 Drawing Sheets

Related U.S. Application Data filed on May 9, 2019, provisional application No. 62/775,116, filed on Dec. 4, 2018.

(51) Int. Cl.
  *H04L 9/32* (2006.01)
  *G16H 15/00* (2018.01)
  *G16H 70/40* (2018.01)
  *G06F 16/248* (2019.01)

(52) U.S. Cl.
  CPC .............. *G16H 15/00* (2018.01); *G16H 70/40* (2018.01); *H04L 9/3247* (2013.01)

(58) Field of Classification Search
  USPC ........................................................ 705/2–3
  See application file for complete search history.

300

| Enter/Edit Regimen Details 310 | Emetogenic Risk: Not Set | | 320 |

Add adverse event
Patient: Suzy Testtest (UNKNOWN)

Basic Information  >  Event details

Clinical trial regimen  ⟵ 402
***Adriamycin 60 mg/m2 /Cytoxan 600 mg/m2 q 2wkx 4 then Taxol 175/m2 q2wkx4 dose dense neulasta ♦

Adverse Event (CTCAE 4.03)  ⟵ 404
None selected  ♦

Search  🔍
Blood and lymphatic system disorders  ⟵ 406

Anemia
A disorder characterized by a reduction in the amount of hemoglobin in 100 ml of blood. Signs and symptoms of anemia may include pallor of the skin and mucous membranes, shortness of breath, palpitations of the heart, soft systolic murmurs, lethargy, and fatigability.  ⟵ 408

Bone marrow hypocellular
A disorder characterized by the inability of the bone marrow to produce hematopoietic elements.

Disseminated intravascular coagulation
A disorder characterized by systemic pathological activation of blood clotting mechanisms which results in clot formation throughout the body. There is an increase in the risk of hemorrhage as the body is depleted of platelets and coagulation factors.

Febrile neutropenia
A disorder characterized by an ANC <1000/mm3 and a single temperature of >38.3 degrees C (101 degrees F) or a sustained temperature of >=38 degrees C (100.4 degrees F) for more than one hour

[Cancel] [Next]
⟵ 410

Add adverse event: Anemia
Patient: Suzy Testtest (UNKNOWN)

⊘ Basic Information  ➤  Event details

A disorder characterized by a reduction in the amount of hemoglobin in 100 ml of blood. Signs and symptoms of anemia may include pallor of the skin and mucous membranes, shortness of breath, palpitations of the heart, soft systolic murmurs, lethargy, and fatigability.

Start date ⟵ 414
[Enter Date] Clear

End date ⟵ 416
[Enter Date] Clear

418

Serious Adverse Event? (?) ⟵ 415
422 ● Yes ○ No

Discontinued study due to AE?
○ Yes ● No ⟵ 420

Baseline?
○ Yes ● No

424

Grade
○ 1: Hemoglobin (Hgb) <LLN – 10.0 g/dL; <LLN – 6.2 mmol/L; <LLN – 100 g/L
● 2: Hgb <10.0 – 8.0 g/dL; <6.2 – 4.9 mmol/L; <100 – 80g/L
○ 3: Hgb <8.0 g/dL; <4.9 mmol/L; <80 g/L; transfusion indicated
○ 4: Life-threatening consequences; urgent intervention indicated
○ 5: Death Relationship to Drugs ⟵ 426
[+] Lorazepam prn
[+] Normal Saline .9%

[Back]                    [Cancel] [Add adverse event]

```
Add adverse event: Anemia
Patient. Suzy Testtest (UNKNOWN)
Relationship to Drugs
  ⊞ Lorazepam prn
  ⊞ Normal Saline .9%
  ⊞ Adriamycin
  ⊞ Cytoxan
  ⊞ Neulasta
  ⊞ Neupogen(G-CSF)
  ⊟ Dexamethasone Phosphate                430                                              432
    Relationship to Dexamethasone Phosphate in Regimen    Action taken with Dexamethasone Phosphate in Regimen
    Clear                                                 Clear
    ○ Unrelated                                           ○ Dose reduced
    ○ Unlikely related                                    ○ Drug interrupted
    ● Possibly related                                    ○ Drug discontinued
    ○ Probably related                                    ● No action taken
    ○ Definitely related                                  ○ Unknown
  ⊞ Dexamethasone Phosphate
  ⊞ Taxol
  ⊞ Emend Tri Pack PRN
Related to
  ○ Concomitant drug treatment

[Back]                                              [Cancel] [Add adverse event]
```

Add adverse event: Anemia
Patient: Suzy Testtest (UNKNOWN)

[+] Dexamethasone Phosphate
[+] Taxol
434 — [+] Emend Tri Pack PRN

Related to
○ Concomitant drug treatment
○ Concomitant non-drug treatment
● Disease under study
○ None
436 — ○ Disease not under study / other

Outcome
○ Recovered / resolved
○ Recovered / resolving
○ Recovered / resolved with sequelae
● Not recovered / resolved
○ Unknown
○ Fatal

Additional notes

[Back]  [Cancel] [Add adverse event]
                                  438

Research
Adverse Events

[Add Adverse Event] [Show all] [Route for Sign Off] — 506

***Adriamycin 60 mg/m2 /Cytoxan 600 mg/m2 q 2wkx 4 then Taxol 175/m2 q2wkx4 dose dense neulasta
CTCAE v4.03 – Date format: MM/DD/YYYY

| Adverse event | Baseline | Serious | Dates | Grade | Causality and action taken | Relationship | Outcome | Discontinued |
|---|---|---|---|---|---|---|---|---|
| Anemia | No | Yes | Start date End Date | 2 | Dexamethasone Phosphate Relationship: Possibly related Action taken: No action taken | Disease under study | Not recovered / resolved | No |
| Anemia | No | Yes | Start date End date | 1 | | Concomitant drug treatment | Recovered / resolved | Yes |

PHASE 1: Weekly Topotecan 2.5-4.0 mg/m2 (D 1,8,15) Q 28 days
CTCAE v4.03 – Date format: MM/DD/YYYY

| Adverse event | Baseline | Serious | Dates | Grade | Causality and action taken | Relationship | Outcome | Discontinued |
|---|---|---|---|---|---|---|---|---|
| Febrile neutropenia | Yes | Yes | Start date 11/03/2018 End Date | | | | | No |
| Anemia | No | Yes | Start date End date | | | | | Yes |

1 event(s) hidden by filters Show all

```
O O O
🔒                                                                    🔍
   Received Requests: (none)
   Sent Requests: New Request
   Archived Requests:
   My Messages (none)
   Direct Messages  Show  New
   Unsigned Documents That I Created (9)  Show
   Review Lab Reports (none)
   Radiology Documents (none)
   Visit Charges to Complete (none)
   Hospital Visits (none)  New Visit
   Alert Messages (none)
   Adverse Events (1 patient)  Hide
   ☐ Testtest, Suzy (UNKNOWN)
   ***Adriamycin 60 mg/m2 /Cytoxan 600 mg/m2 q 2wkx 4 then Taxol 175/m2 q2wkx4 dose dense neulasta
   CTCAE v4.03 – Date format: MM/DD/YYYY
```

510

| Adverse event | Baseline | Serious | Dates | Grade | Causality and action taken | Relationship | Outcome | Discontinued |
|---|---|---|---|---|---|---|---|---|
| ⊞ Anemia | No | Yes | Start date End Date | 2 | Dexamethasone Phosphate Relationship: Possibly related Action taken: No action taken | Disease under study | Not recovered / resolved | No |
| Assigned to zAltos-Sutton, Lauren by zAltos-Sutton, Lauren 11/20/2018 | | | | | | | | |
| Created by zAltos-Sutton, Lauren 11/20/2018 | No | Yes | Start date End Date | 2 | Dexamethasone Phosphate Relationship: Possibly related Action taken: No action taken | Disease under study | Not recovered / resolved | No |
| ⊞ Anemia | No | Yes | Start date End Date | 1 | | Concomitant drug treatment | Recovered / resolved | Yes |

Research
Adverse Events

[Add Adverse Event] [Show all] [Route for Sign Off]

***Adriamycin 60 mg/m2 /Cytoxan 600 mg/m2 q 2wkx 4 then Taxol 175/m2 q2wkx4 dose dense neulasta
CTCAE v4.03 -- Date format: MM/DD/YYYY

| | Adverse event | Baseline | Serious | Dates | Grade | Causality and action taken | Relationship | Outcome | Discontinued |
|---|---|---|---|---|---|---|---|---|---|
| ⊞ | Anemia | No | Yes | Start date<br>End Date | 2 | Dexamethasone Phosphate<br>Relationship: Possibly related<br>Action taken: No action taken | Disease under study | Not recovered / resolved | No |
| Assigned to zAltos-Sutton, Lauren by zAltos-Sutton, Lauren<br>11/20/2018 | | | | | | | | | |
| Created by zAltos-Sutton, Lauren<br>11/20/2018 | | No | Yes | Start date<br>End Date | 2 | Dexamethasone Phosphate<br>Relationship: Possibly related<br>Action taken: No action taken | Disease under study | Not recovered / resolved | No |
| ⊞ | Anemia | No | Yes | Start date<br>End Date | 1 | | Concomitant drug treatment | Recovered / resolved | Yes |

PHASE 1: Weekly Topotecan 2.5-4.0 mg/m2 (D 1,8,15) Q 28 days
CTCAE v4.03 -- Date format: MM/DD/YYYY

| | Adverse event | Baseline | Serious | Dates | Grade | Causality and action taken | Relationship | Outcome | Discontinued |
|---|---|---|---|---|---|---|---|---|---|
| ⊞ | Febrile neutropenia | Yes | Yes | Start date<br>11/03/2018<br>End Date | | | | | No |

| | Drugs | Script date | Stop date | Instructions | Verified |
|---|---|---|---|---|---|
| ☐ | Zofran 4 mg tab | 12/31/2017 | 01/31/2018 | 1 p.o.q. day | |
| ☐ | TETRACYCLINE 500MG CAP | 12/01/2017 | 12/05/2017 | 1 p.o.q. day | 01/03/2018 |
| ☐ | Zofran 4 mg tab | 11/30/2017 | 12/30/2017 | 1 p.o.q. day | 01/03/2018 |

Import medications from summary pages
Patient: John Smith (123456)

Previously imported medication(s) will not be selectable.
Medications

708

Cancel

| | |
|---|---|
| Inbox ✉<br>Search 🔍 | John Smith<br>ROOM: Exam Room 1 ▾  SEX: [Sex]   MRN: #123456   MD: [MD Name]<br>MEMO: This patient has a copay of $40 and no know allergies documented. |
| GENERAL<br>Visit lists<br>Scheduler<br>Reports<br>New task<br>PATIENT CHART<br>Demographics<br>Summary<br>Documents<br>Treatment plan<br>InHouse Rx<br>Orders<br>Visit notes<br>Referrals<br>Text note<br>Research | Research<br>Adverse Events   Concomitant Medications   Past Medical/Surigal History<br><br>[Add medication] [Import from summary page]                         🔍<br>Metastatic Colon:  Capecitabine,Irinotecan,Cetuximab<br>CTCAE v4.03<br><br>\| ☐ \| Medication \| Start date \| End date \| Dose \| Route \| Frequency \| Formulation \| Indication ⓘ \|<br>\| ☐ \| > Zofran \| 2017 Nov 24 \| 2017 Dec 24 \| 4mg \| Oral \| PRN When experiencing symptoms \| Capsule \| Nausea (2017 Nov 22 -- 2017 Dec 24) Dyspepsia (2017 Jan 03 -- ongoing) Concomitant procedure: Blood draw \| |

| | |
|---|---|
| Inbox ✉ | John Smith |
| Search 🔍 | ROOM: Exam Room 1 ▼  SEX: [Sex]  MRN: #123456  MD: [MD Name] |
| | MEMO: This patient has a copay of $40 and no know allergies documented. |

GENERAL
Visit lists
Scheduler
Reports
New task

PATIENT CHART
Demographics
Summary
Documents
Treatment plan
InHouse Rx
Orders
Visit notes
Referrals
Text note
Research

Research

Adverse Events    Concomitant Medications    Past Medical/Surigal History

[ Add medication ] [ Import from summary page ]                              🔍 [ Show all ]

Metastatic Colon: Capecitabine,Irinotecan,Cetuximab
CTCAE v4.03

| | Medication | Start date | End date | Dose | Route | Frequency | Formulation | Indication ⓘ |
|---|---|---|---|---|---|---|---|---|
| ☐ | > Zofran | 2017 Nov 24 | 2017 Dec 24 | 4mg | Oral | PRN | Capsule | Nausea (2017 Nov 22 -- 2017 Dec 24) Dyspepsia (2017 Jan 03 -- ongoing) Concomitant procedure: Blood draw |
|   | Edited by Doe, Jane 2018 Jan 23 11:45 am | 2017 Nov 24 | 2017 Dec 24 | 4mg | Oral | PRN | Capsule | Nausea (2017 Nov 22 -- 2017 Dec 24) Dyspepsia (2017 Jan 03 -- ongoing) Concomitant procedure: Blood draw |
|   | Created by Doe, Jane 2018 Jan 23 11:32 am | | | | | | | |
| ☐ | > Tylenol 8 Hour | 2017 Nov 27 | | 325mg | Oral | QD PRN | Tablet | |
| ☐ | > Ibuprofen | 01/15/2018 | 01/25/2018 | 200ng | Oral | | Tablet | |

— 1002 (left callout)
— 1004 (right callout)

John Smith
ROOM: Exam Room 1 · SEX: (Sex) · MRN: #123456 · MD: (MD Name)
MEMO: This patient has a copay of $40 and no known allergies documented.

GENERAL
Visit list
Scheduler
Reports
New task

PATIENT CHART
Demographics
Summary
Documents
Treatment plan
In-house Rx
Orders
Visit notes
Referrals
Text note
Research

Research
Adverse Events

Add medical
No past medica

Add past medical or surgical history
Patient: John Smith (123456)

Start date
| Year | Month | Day | 📅 |

End date
| Year | Month | Day | 📅 |

Grade
○ 1
○ 2
○ 3
○ 4
○ 5
○ N/A

Outcome ─╱⁻1212
○ Ongoing
○ Resolved
                    ╱⁻1214
Concomitant medication taken
○ Yes
○ No

[Cancel] [Add medical history]
                            ╲
                             1216

| Inbox 🔍 | John Smith |
| Search 🔍 | ROOM: Exam Room 1 ▼  SEX: [Sex]   MRN: #123456   MD: [MD Name] |
| | MEMO: This patient has a copay of $40 and no know allergies documented. |

GENERAL
Visit lists
Scheduler
Reports
New task

PATIENT CHART
Demographics
Summary
Documents
Treatment plan
InHouse Rx
Orders
Visit notes
Referrals
Text note
Research

Research

Adverse Events    Concomitant Med    Past Med History

[ Add medical history ]

Metastatic Colon:  Capecitabine,Irinotecan,Cetuximab

Date format: YYYY  MMM  DD

| Past medical condition or surgical history | Grade | Start date | End date | Outcome | Con med |
|---|---|---|---|---|---|
| ▼ Right Knee Replacement | N/A | 2015 Jan 23 | 2015 Jan 23 | Resolved | Yes |

FIG. 13

SYSTEMS AND METHODS FOR TRACKING PATIENT EVENTS

CROSS REFERENCES TO RELATED APPLICATIONS

This application claims the benefit of priority of U.S. Provisional Application No. 62/775,116, filed on Dec. 4, 2018, U.S. Provisional Application No. 62/845,581, filed May 9, 2019, and U.S. Provisional Application No. 62/850,069, filed May 20, 2019. The entire contents of the foregoing applications are incorporated herein by reference in their entirety.

BACKGROUND

Technical Field

The present disclosure relates to systems and methods for tracking patient events.

Background Information

Numerous data points are often used to evaluate the efficacy of trial regimens. However, tools to collect patient data can be cumbersome or lead to inaccurate recording of data. For example, paper-based systems are often used to record adverse events reported by patients. These paper-based systems require providers to retroactively enter adverse event data based on handwritten notes. Thus, not all data points may be captured in a timely or accurate manner as there are numerous opportunities for error.

Accordingly, there is a need for a point of care solution that enables the capture of adverse event data with minimal disruption to physician workflow and a better user experience. Such a point of care solution would facilitate timely and accurate data collection, thereby enabling retrospective analysis of the efficacy of trial regimens.

SUMMARY

Embodiments consistent with the present disclosure include systems and methods for tracking adverse events. In an embodiment, a system for tracking adverse events may comprise at least one processing device. The at least one processing device may be programmed to: receive a request from a user to record an adverse event experienced by a patient; receive a search term input by the user; identify, in an adverse event database and based on the search term, at least one database record for an adverse event, wherein the at least one database record includes an adverse event type and at least one characteristic; receive, via an input field, a rating of the at least one characteristic for the patient; generate an adverse event record based on the adverse event type and the rating; and store the adverse event record in an adverse event log.

In an embodiment, a method for tracking adverse events may comprise receiving a request from a user to record an adverse event experienced by a patient; receive a search term input by the user; identifying, in an adverse event database and based on the search term, at least one database record for an adverse event, wherein the at least one database record includes an adverse event type and at least one characteristic; receiving, via an input field, a rating of the at least one characteristic for the patient; generating an adverse event record based on the adverse event type and the rating; and storing the adverse event record in an adverse event log.

In an embodiment, a system for tracking medical information associated with a patient may comprise at least one processing device. The at least one processing device may be programmed to: receive a request from a user to add a medication to a patient history record associated with the patient; receive a search term input by the user; retrieve, via an application programming interface, at least one medication record associated with the search term; receive a selection of a medication from the at least one medication records; receive input indicative of at least one of: a dose, a formulation, a frequency, and a route associated with the selected medication; and update the patient history record with the selected medication and the received input.

In an embodiment, a method for tracking medical information associated with a patient may comprise: receiving a request from a user to add a medication to a patient history record associated with the patient; receive a search term input by the user; retrieving, via an application programming interface, at least one medication record associated with the search term; receiving a selection of a medication from the at least one medication records; receiving input indicative of at least one of: a dose, a formulation, a frequency, and a route associated with the selected medication; and updating the patient history record with the selected medication and the received input.

Consistent with other disclosed embodiments, non-transitory computer readable storage media may store program instructions, which are executed by at least one processing device and perform any of the methods described herein.

BRIEF DESCRIPTION OF THE DRAWINGS

The accompanying drawings, which are incorporated in and constitute part of this specification, and together with the description, illustrate and serve to explain the principles of various exemplary embodiments. In the drawings:

FIG. 3 is an illustration of an exemplary graphical user interface (GUI) consistent with the present disclosure.

FIGS. 4A-4D are illustrations of exemplary GUIs consistent with the present disclosure.

FIGS. 5A, 5B, and 5C are illustrations of exemplary GUIs consistent with the present disclosure.

FIGS. 7A and 7B are illustrations of exemplary GUIs consistent with the present disclosure.

FIGS. 9A-9F are illustrations of exemplary GUIs consistent with the present disclosure.

FIGS. 10A and 10B are illustrations of exemplary GUIs consistent with the present disclosure.

FIGS. 12A and 12B are illustrations of exemplary GUIs consistent with the present disclosure.

FIG. 13 is in illustration of an exemplary GUI consistent with the present disclosure.

DETAILED DESCRIPTION

Figure 1:
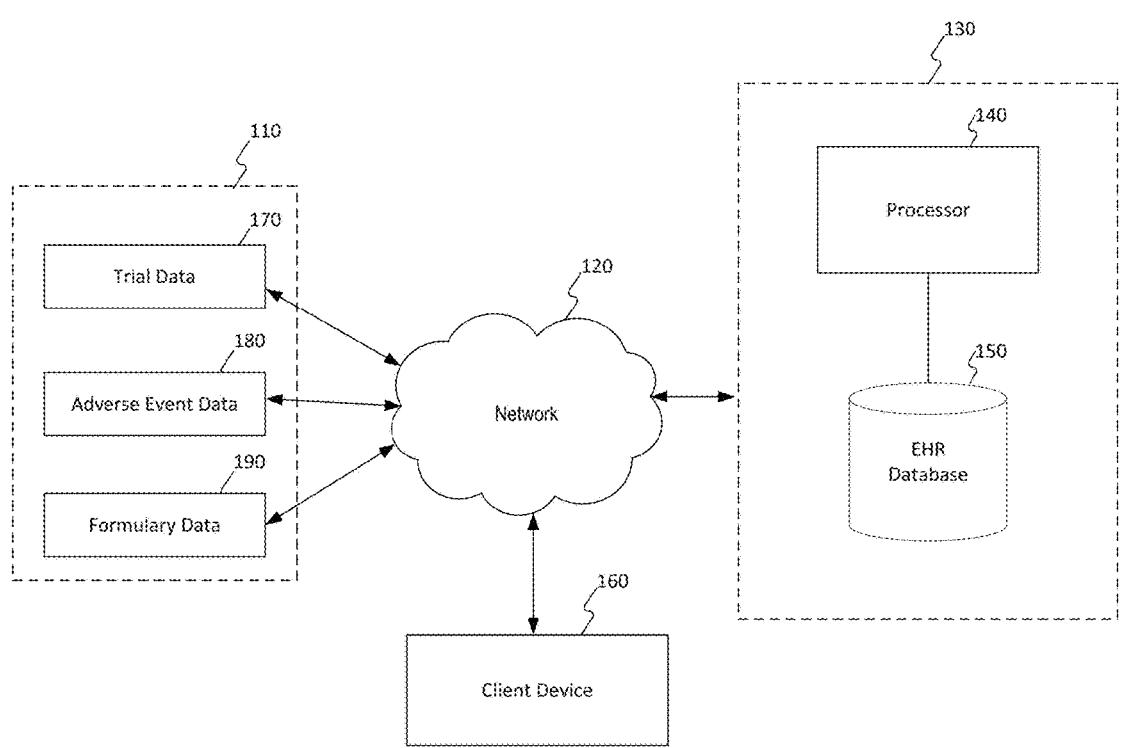
FIG. 1 is a block diagram illustrating an exemplary system environment for implementing embodiments consistent with the present disclosure.

The following detailed description refers to the accompanying drawings. Wherever possible, the same reference numbers are used in the drawings and the following description to refer to the same or similar parts. While several illustrative embodiments are described herein, modifications, adaptations and other implementations are possible. For example, substitutions, additions or modifications may be made to the components illustrated in the drawings, and the illustrative methods described herein may be modified by substituting, reordering, removing, or adding steps to the disclosed methods. Accordingly, the following detailed description is not limited to the disclosed embodiments and examples. Instead, the proper scope is defined by the appended claims.

Embodiments herein include computer-implemented methods, tangible non-transitory computer-readable mediums, and systems. The computer-implemented methods may be executed, for example, by at least one processor (e.g., a processing device) that receives instructions from a non-transitory computer-readable storage medium. Similarly, systems consistent with the present disclosure may include at least one processor (e.g., a processing device) and memory, and the memory may be a non-transitory computer-readable storage medium. As used herein, a non-transitory computer-readable storage medium refers to any type of physical memory on which information or data readable by at least one processor may be stored. Examples include random access memory (RAM), read-only memory (ROM), volatile memory, nonvolatile memory, hard drives, CD ROMs, DVDs, flash drives, disks, and any other known physical storage medium. Singular terms, such as "memory" and "computer-readable storage medium," may additionally refer to multiple structures, such a plurality of memories and/or computer-readable storage mediums. As referred to herein, a "memory" may comprise any type of computer-readable storage medium unless otherwise specified. A computer-readable storage medium may store instructions for execution by at least one processor, including instructions for causing the processor to perform steps or stages consistent with an embodiment herein. Additionally, one or more computer-readable storage mediums may be utilized in implementing a computer-implemented method. The term "computer-readable storage medium" should be understood to include tangible items and exclude carrier waves and transient signals.

Embodiments of the present disclosure provide systems and methods for tracking adverse events and/or tracking medical information associated with a patient. A user of the disclosed systems and methods may encompass any individual who may wish to access a patient's clinical experience and/or analyze patient data. Thus, throughout this disclosure, references to a "user" of the disclosed systems and methods may encompass any individual, such as a physician, a quality assurance department at a health care institution, and/or the patient. While reference is made to tumors or cancer therapies throughout this disclosure, these are provided as an example only, and it is understood that the disclosed systems and methods may apply to various other diseases and/or treatments.

Disclosed embodiments describe a point of care solution for tracking adverse events and medical history of patients associated with a trial or follow-up regimen. For example, the user interface may be the means through which a physician may record adverse events, medical history, and/or concomitant medications of a patient within the physician workflow, thereby improving efficiency and providing a seamless process. Traditionally, adverse events and related information is recorded in paper files and may later be transcribed into a system. This method of recording adverse events is inefficient and may result in inaccuracies if the data is not eventually recorded digitally, or if the data is transcribed incorrectly. Disclosed embodiments may provide an application that seamlessly captures patient data points, which may, in turn, provide a complete and accurate dataset for trial evaluation.

FIG. 1 illustrates an exemplary system environment 100 for implementing embodiments consistent with the present disclosure, described in detail below. As shown in FIG. 1, system environment 100 includes several components. It will be appreciated from this disclosure that the number and arrangement of these components is exemplary and provided for purposes of illustration. Other arrangements and numbers of components may be used without departing from the teachings and embodiments of the present disclosure.

As shown in FIG. 1, exemplary system environment 100 includes a system 130. System 130 may include one or more server systems, databases, and/or computing systems configured to receive information from entities over a network, process the information, store the information, and display/transmit the information to other entities over the network. Thus, in some embodiments, the network may facilitate cloud sharing, storage, and/or computing. In one embodiment, system 130 may include a processor 140 and one or more databases 150 (e.g., an electronic health record (EHR) database), which are illustrated in a region bounded by a dashed line representing system 130 in FIG. 1. Processor 140 may comprise at least one processing device, such as one or more generic processors, e.g., a central processing unit (CPU), a graphics processing unit (GPU), or the like and/or one or more specialized processors, e.g., an application-specific integrated circuit (ASIC), a field-programmable gate array (FPGA), or the like.

In one embodiment, system 130 may transmit and/or receive data to/from various other components, such as one or more data sources 110 and client device 160. More specifically, system 130 may be configured to receive and store the data transmitted over a network 120 (e.g., the Internet, an Intranet, WAN, LAN, cellular network, Bluetooth, etc.) from various data sources, including data sources 110, process the received data, and transmit data and results based on the processing to client device 160.

The various components of system environment 100 may include an assembly of hardware, software, and/or firmware, including a memory, a central processing unit (CPU), and/or a user interface. Memory may include any type of RAM or ROM embodied in a physical storage medium, such as magnetic storage including floppy disk, hard disk, or magnetic tape; semiconductor storage such as solid-state disk (SSD) or flash memory; optical disc storage; or magneto-optical disc storage. A CPU may include one or more processors for processing data according to a set of programmable instructions or software stored in the memory. The functions of each processor may be provided by a single dedicated processor or by a plurality of processors. Moreover, processors may include, without limitation, digital signal processor (DSP) hardware, or any other hardware capable of executing software. An optional user interface may include any type or combination of input/output devices, such as a display monitor, keyboard, and/or mouse.

Data transmitted and/or exchanged within system environment 100 may occur over a data interface. As used herein, a data interface may include any boundary across which two or more components of system environment 100 exchange data. For example, environment 100 may exchange data between software, hardware, databases, devices, humans, or any combination of the foregoing. Furthermore, it will be appreciated that any suitable configuration of software, processors, data storage devices, and networks may be selected to implement the components of system environment 100 and features of related embodiments.

As described further below, system 130 may be configured to receive trial data 170, e.g., data indicating available trials at a provider location, and/or adverse event data, e.g., a data dictionary such as the Common Terminology Criteria for Adverse Events (CTCAE) published by the National Institutes of Health (NIH), from data sources 110 or other sources in network 120. Data sources 110 may include a variety of sources of medical, terminology, and administrative data.

Trial data 170 may be data received from a provider or medical personnel, e.g., hospital administrator. The trial data may indicate one or more ongoing trials at the provider location. In some embodiments, trial data for a particular patient may be provided as part of the patient's electronic health record (EHR). Trial data 170 may be received from an administrative system, e.g., a hospital system or hospital database and may be represented as one or more electronic files, such as text files, portable document format (PDF) files, extensible markup language (XML) files, or the like. If the documents are stored as PDF files, images, or other files without text, the electronic data representations may also include text associated with the documents derived from an optical character recognition process.

In some embodiments, adverse event data 180 may be received from a standards or terminology publisher, e.g., NIH. Adverse event data 180 may include a structured and/or non-structured data defining a number of adverse events and a number of grades for each adverse event. In some embodiments, one or more adverse event documents may be collated and/or stored in the same database. In other embodiments, one or more adverse event documents may be distributed across a plurality of databases. In some embodiments, the adverse events may be stored and/or provided a plurality of electronic data representations. For example, the adverse events may be represented as one or more electronic files, such as text files, portable document format (PDF) files, extensible markup language (XML) files, or the like. If the documents are stored as PDF files, images, or other files without text, the electronic data representations may also include text associated with the documents derived from an optical character recognition process.

In some embodiments, formulary data 190 may be received from a standards or formulary publisher, e.g., the Clinical Data Interchange Standards Consortium (CDISC). In another embodiment, formulary data 190 may be stored in a local or remote formulary database. Formulary data 190 may include a structured and/or non-structured data defining a number of properties of a set of drugs. In some embodiments, one or more formulary documents may be collated and/or stored in the same database. In other embodiments, one or more formulary documents may be distributed across a plurality of databases. In some embodiments, the formulary information may be stored and/or provided a plurality of electronic data representations. For example, the formulary data may be represented as one or more electronic files, such as text files, portable document format (PDF) files, extensible markup language (XML) files, or the like. If the documents are stored as PDF files, images, or other files without text, the electronic data representations may also include text associated with the documents derived from an optical character recognition process.

System 130 may be, for example, an EHR system and may include an EHR database 150. EHR database 150 may store patient EHR records, where each patient may be associated with one or more records generated by one or more health care professionals or by the patient. For example, a doctor associated with the patient, a nurse associated with the patient, a physical therapist associated with the patient, or the like, may generate an EHR for the patient. In some embodiments, one or more records may be collated and/or stored in the same database. In other embodiments, one or more records may be distributed across a plurality of databases. In some embodiments, the records may be stored and/or provided a plurality of electronic data representations. For example, the EHRs may be represented as one or more electronic files, such as text files, portable document format (PDF) files, extensible markup language (XML) files, or the like. If the documents are stored as PDF files, images, or other files without text, the electronic data representations may also include text associated with the documents derived from an optical character recognition process. In some embodiments, a patient EHR may include, for example, identification information (e.g., name, address, date of birth, etc.), medical history information (e.g., treatment dates, surgical history, prescribed medicines, family medical history, etc.), provider information (e.g., primary insurance provider, copay amount, secondary insurance provider), and/or contact information (e.g., emergency contact information, primary care provider contact information, etc.).

System 130 may further communicate with one or more client devices 160 over network 120. For example, system 130 may be configured to receive input from client device 160 indicative of a trial regimen, adverse event, medical event, and/or concomitant medication to add to a patient EHR. Client device 160 may include any entity or device capable of receiving or transmitting data over network 120. For example, client device 160 may include a computing device, such as a server or a desktop or laptop computer. Client device 160 may also include other devices, such as a mobile device, a tablet, a wearable device (i.e., smart watches, implantable devices, fitness trackers, etc.), a virtual machine, an IoT device, or other various technologies. In some embodiments, client device 160 may transmit queries for information about an adverse event over network 120 to system 130, such as a query for a particular adverse event or trial regimen. In embodiments in which EHR database 150 is a remote database, system 130 may transmit queries via network 120 to retrieve, create, edit, or delete EHR information associated with a patient.

Figure 2:
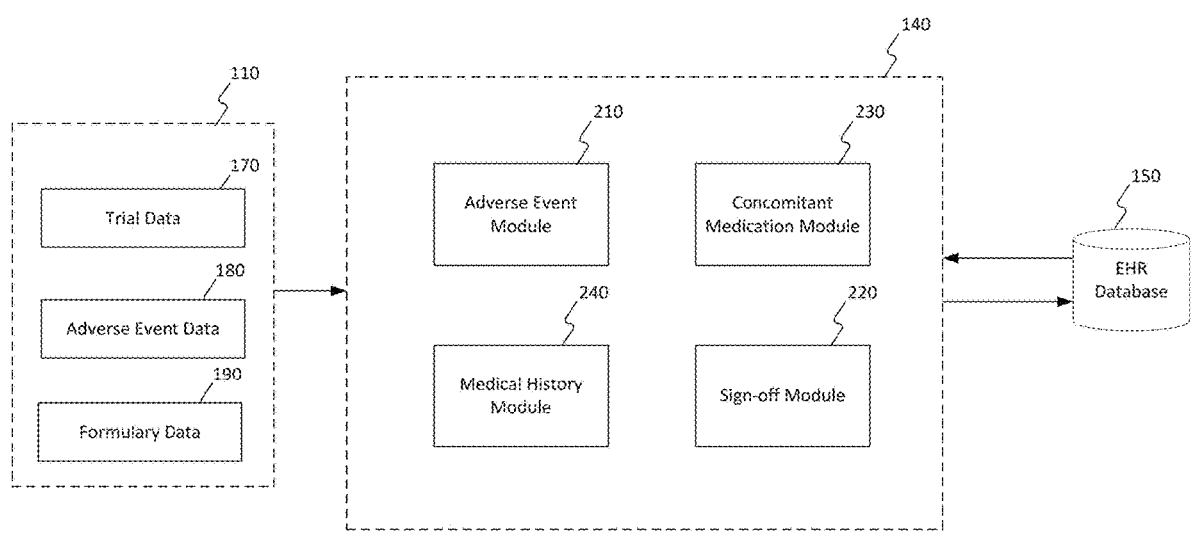
FIG. 2 is a block diagram illustrating an exemplary process for implementing embodiments consistent with the present disclosure.

FIG. 2 illustrates system 200, which is an exemplary embodiment of system 130 for implementing embodiments consistent with the present disclosure. System 200 may be implemented as part of system 130 (FIG. 1). For example, system 200 be a component or process of processor 140. System 130 may be configured to enable seamless data capture in a physician workflow.

Adverse event module 210 may be configured to receive input, via a graphical user interface (GUI) displayed on client device 160, indicative of a trial regimen to associate with a patient. In some embodiments, adverse event module may receive trial data 170 indicative of currently active trials at the provider location or practice. A GUI may be configured to display a selectable list of active trials or may receive a search term. In some embodiments, adverse event module may query a trial database to identify active trials matching the received search term. After receiving a selection of a trial regimen, adverse event module 210 may generate an update to the patient's EHR in EHR database 150.

Adverse event module 210 may be further configured to receive a search term, input via client device 160, associated with an adverse event. Adverse event module 210 may be configured to query an adverse event database storing adverse event data 180. In some embodiments, adverse event module 210 may query an adverse event database and return a at least one record containing the search term associated with an adverse event. In another embodiment, adverse event module 210 may determine a relevance score associated with each adverse event record based on, for example, a number of times the search term appears in the record, or whether the record contains a partial match of the search term.

Adverse event module 210 may be configured to transmit instructions to client device 160 to cause the device to display a list of selectable search results. Upon receiving, from a user, a selection of an adverse event, adverse event module 210 may generate, based on data associated with the adverse event, a GUI configured to receive further detail regarding the adverse event. For example, the GUI may be configured to receive an indication of the seriousness of the adverse event, a grade associated with the adverse event (e.g., on a scale of 1-5), a relatedness of the adverse event to a drug associated with the selected regimen, and the like.

After receiving, from client device 160, additional adverse event information, adverse event module 210 may update the patient's EHR in EHR database 150. In some embodiments, an adverse event added to a patient EHR may be required to receive a sign-off from a supervisor or provider. In these embodiments, the adverse event may be stored in the patient's EHR with an unsigned status.

In some embodiments, sign-off module 220 may be configured to receive an unsigned adverse event from adverse event module 210. Sign-off module 220 may generate a log of unsigned events and provide an indication of the unsigned adverse event to the supervisor whose signature is required. In some embodiments, the supervisor may receive an alert, via client device 160, that an adverse event requires his review and signature. Sign-off module 220 may compile and store and audit log of adverse event records. The audit log may be stored in a database of system 130 or in a remote database.

In some embodiments, sign-off module 220 may also be configured to receive unsigned medical history records generated by medical history module 240 and unsigned medication records generated by concomitant medication module 230.

Concomitant medication module 230 may be configured to receive input, e.g., from a client device 160, that a user wishes to add a concomitant medication to a patient's EHR. Concomitant medication data may be received, for example, with trial data 170, where concomitant medications are associated with one or more trial regimens. In some embodiments, the user may select, via a GUI displayed on client device 160, a trial regimen. The user may then select to add a medication associated with the regimen to the patient's EHR. The user may select the drug, for example, from a pre-populated drop-down menu or table displaying the drugs associated with the trial regimen.

Concomitant medication module 230 may be configured to access, via an application programming interface (API), formulary data 190. Concomitant medication module 230 may query, via the API, a formulary database to retrieve formulary information associated with the selected drug. The formulary information may include, for example, available dosages, formulations, routes, and/or frequencies. Concomitant medication module 230 may be configured to display the formulary information via a GUI displayed on client device 160. For example, the GUI may include one or more radio buttons, sliders, drop-down menus, text input boxes, checkboxes, and the like, configured to receive input indicating information about the administered concomitant medication. For example, the user may be presented with a list of available dosages of the selected drug and may select a radio button indicating the administered dosage.

Concomitant medication module 230 may be further configured to receive an indication associated with the selected drug. The indication may be, for example, a previously recorded adverse event stored in the patient's EHR. Concomitant medication module 230 may be configured to retrieve, from EHR database 150, one or more adverse event records associated with the patient. The adverse event records may be displayed to the user as, for example, a drop-down menu. After receiving a selection of the adverse event and/or formulary information, concomitant medication interface 230 may update the patient's EHR record with the concomitant medication information.

System 130 may further include a medical history module 240 configured to receive information associated with a past medical event experienced by the patient. Medical history module 240 may be configured to receive either a structured or non-structured search term associated with an event type, e.g., a CTCAE adverse event type. Medical history module 240 may be configured to query an adverse event or event database storing adverse event data 180. In some embodiments, medical history module 240 may query an adverse event database and return a at least one record containing the search term associated with an adverse event. In another embodiment, medical history module 240 may determine a relevance score associated with each adverse event record based on, for example, a number of times the search term appears in the record, or whether the record contains a partial match of the search term.

Medical history module 240 may be configured to provide a list of selectable search results to the user via a GUI displayed on client device 160. Medical history module 240 may be configured to receive, via the GUI, additional information associated with the medical event. Additional information may include, a start date, an end date, an outcome (e.g., if the event is resolved or on-going), a grade associated with the event, and the like.

FIGS. 3, 4A-4D, and 5A-5C illustrate exemplary graphical user interfaces (GUIs) for tracking adverse events consistent with disclosed embodiments. The GUIs of FIGS. 3, 4A-4D, and 5A-5C may be displayed to a user via client device 160, which may be capable of receiving user input via a keyboard, microphone, touchscreen, or other I/O device.

Figure 3:
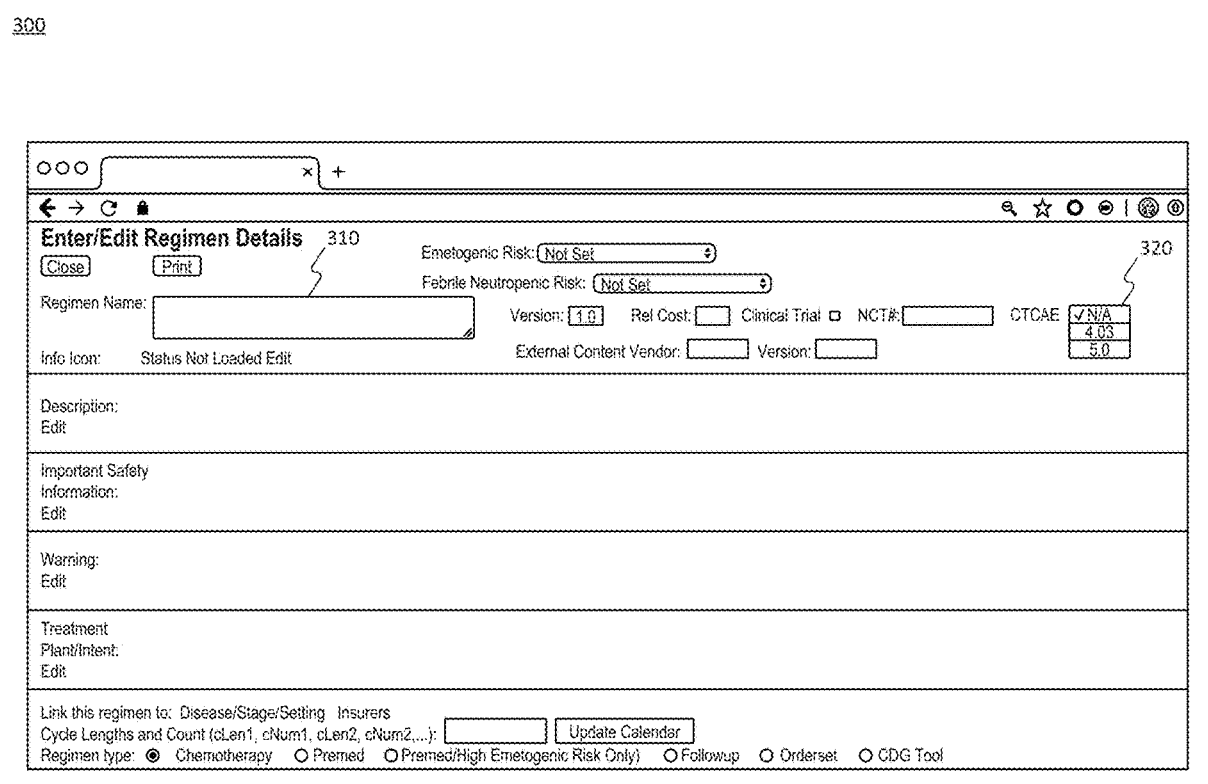

FIG. 3 is an exemplary GUI 300 of a portal through which to add a regimen to an electronic health record (EHR) for a patient. GUI 300 may be associated with an EHR system, e.g., system 130. GUI 300 may be configured to display, via drop-down list 310, one or more trial regimens available at the provider location or practice. A user may select a regimen from drop-down list 310 and may also select, from a drop-down menu 320, a CTCAE version. The selected CTCAE version may determine which version of an adverse events database is queried by adverse event module 210 and/or medical history module 240.

FIG. 4A is an exemplary GUI 400 of a portal for adding an adverse event to a patient's EHR. GUI 400 may display a drop-down menu 402 of regimens associated with the patient, e.g., regimens added to the patient EHR via GUI 300. The user may add an adverse event by either selecting a pre-populated adverse event or searching an adverse event database. The pre-populated adverse events and the adverse event database may correspond to the version selected when the regimen was added to the patient's EHR. In some embodiments, drop-down list 404 may display a list of adverse event categories, where each category is associated with an adverse event. For example, in the adverse event database, one or more adverse events may be associated with a category. In other embodiments, drop-down list 404 may display a list of adverse events stored in the adverse event database. In some embodiments, the user may select an adverse event or adverse event category from drop-down menu 404. In another embodiment, the user may search the adverse event database by entering a search term in text box 406.

GUI 400 may be configured to display a list of selectable adverse events associated with a search term or an adverse event category selected from drop-down list 404. For example, GUI 400 may display a list 408 of search results, where the search results include adverse events whose descriptions or names include the search term. In another embodiment, GUI 400 may display a list of the adverse events associated with the selected adverse event category. The list 408 may display adverse events and other information associated with each adverse event, e.g., a description, retrieved from the adverse event database.

The user may select an adverse event and select the "Next" button 410 to generate GUI 412 shown in FIG. 4B. GUI 412 may be configured to display a number of input fields associated with the adverse event. For example, GUI 412 may be configured to receive a start date 414, an end date 416, an indication of whether the adverse event was a serious event 418, whether the study was discontinued due to the adverse event 420, a baseline indication 422, and/or a grade of the experienced adverse event 424. Input fields 414-424 may be configured to receive input from the user in a number of ways, for example, using radio buttons, checkboxes, text boxes, and the like.

In some embodiments, GUI 412 may be configured to provide one or more definitions to the user to facilitate proper data entry. For example, by hovering over icon 415 with a cursor or making a selection vi a touchscreen, the GUI 412 may display to the user a clinical definition of a serious adverse event. In another embodiment, grades 1 through 5 may be displayed with a description of one or more clinical attributes associated with the grade. These descriptions may be, for example, retrieved from an adverse event database by adverse event module 210.

GUI 412 may also provide a list of drugs 426 associated with the selected regimen. The user add information regarding the adverse event to a specific drug of the regimen by clicking on an icon or the drug name to expand the window. FIG. 4C, is another view of GUI 412 showing the full list 426 of drugs associated with the selected regimen.

In FIG. 4C, section 428, associated with dexamethasone phosphate, has been expanded. The expanded area may display additional, drug-specific input fields. For example, GUI 412 may be configured to receive input indicative of the relationship of the adverse event to the drug in the regimen 430 and/or an indication of whether an action was taken with the drug 432 (e.g., modifying the dosage, frequency, etc.).

FIG. 4D provides another view of GUI 412, consistent with disclosed embodiments. GUI 412 may be configured to receive additional input, e.g., via touchscreen or other I/O component of client 160, indicating the relation of the adverse event to a condition of the patient 434 (e.g., whether the adverse event is related to a concomitant drug treatment, concomitant non-drug treatment, disease under study, disease not under study, or whether the adverse event is unrelated). GUI 412 may also receive input indicative of an outcome of the adverse event 436.

After receiving the input described with reference to FIGS. 4A-4D, the user may select the "Add adverse event" button 438 shown in FIG. 4D to update the patient EHR with the adverse event and the received input. In some embodiments, a subset of the above-described inputs may be required in order for the user to add the adverse event to the patient's EHR. When the adverse event is added to the patient EHR, it may be stored with an unsigned status. After the adverse event has been added to the patient's EHR, system 130 may display the adverse event 502 on the patient portal, via GUI 500, as shown in FIG. 5A. GUI 500 may also display an indication, e.g., icon 504, that the adverse event has a status of "unsigned." GUI 500 may also display previously recorded adverse events associated with previous regimens.

The user may submit any unsigned adverse event records for sign-off, e.g., by a supervisor, by selecting the "Route for Sign Off" button 506. When the user selects "Route for Sign Off," sign off button 506, module 220 may be configured to receive or retrieve the patient's EHR and/or adverse event data associated with the patient. A supervisor may sign off on an adverse event via GUI 508, shown in FIG. 5B.

As shown in FIG. 5B, GUI 508 may be configured to display one or more adverse event records 510 that have been routed to the supervisor for sign-off. GUI 508 may display additional information about each adverse event including a provider who created the adverse event record and a provider to whom the record is assigned for sign off.

In some embodiments, via GUI 508, the supervisor may electronically sign and date each adverse event record. In some embodiments, prior to inputting a signature, sign off module 220 may be configured to require the supervisor to enter one or more authentication credentials. If the provided credentials are valid and the supervisor is authenticated, the supervisor may then digitally sign and date the adverse event record. After an adverse event record has been signed off, the adverse event may be displayed on a patient's EHR (e.g., adverse event 502) without an icon (e.g., icon 504) or other indication that the record requires sign off, as shown in FIG. 5C.

FIGS. 6, 7A, 7B, 8, 9A-9F, 10A, and 10B illustrate exemplary graphical user interfaces (GUIs) for tracking concomitant medication consistent with disclosed embodiments. The GUIs of FIGS. 6, 7A, 7B, 8, 9A-9F, 10A, and 10B may be displayed to a user via client device 160, which may be capable of receiving user input via keyboard, microphone, touchscreen, or other I/O device.

Figure 6:
FIG. 6 is in illustration of an exemplary GUI consistent with the present disclosure.

FIG. 6 illustrates a GUI 600 displaying a patient EHR. The user may select the "Add medication" button 602 to add a concomitant medication to the patient's EHR. For example, selecting "Add medication" may initiate the process described above with reference to concomitant medication module 230.

Figure 7A:
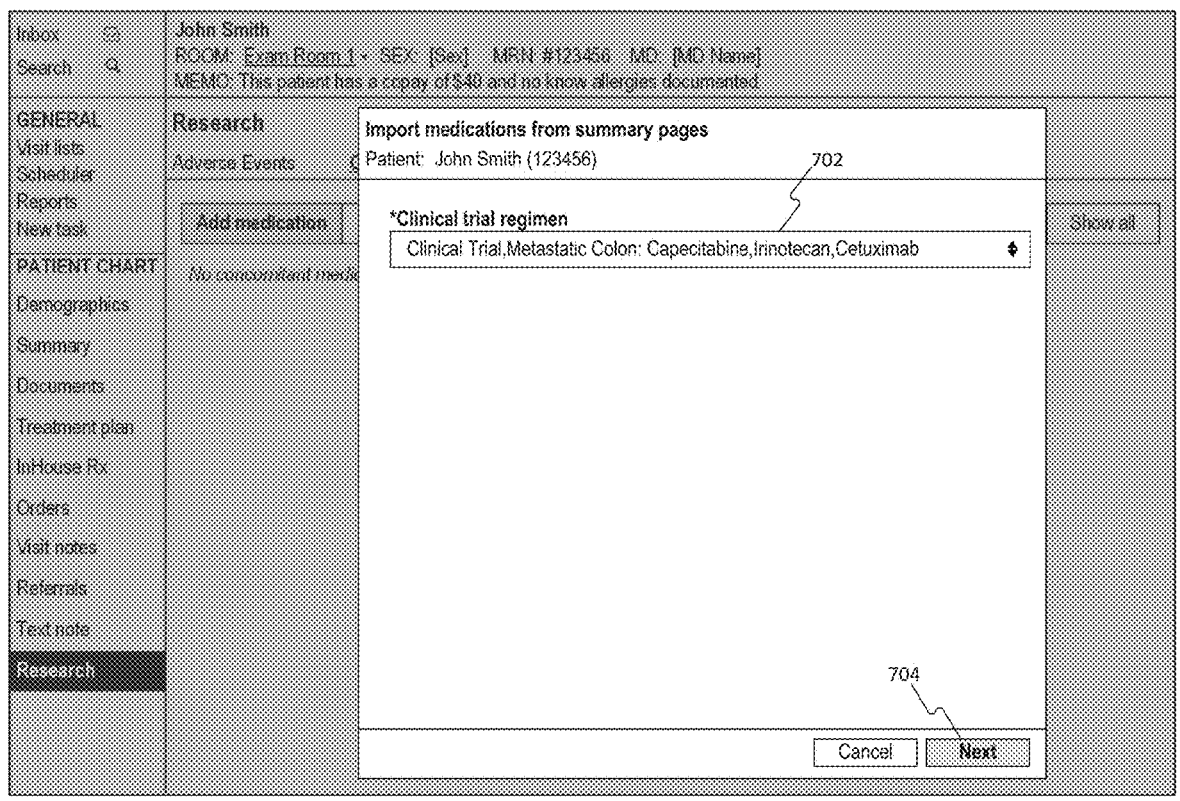
Figure 8:
FIG. 8 is in illustration of an exemplary GUI consistent with the present disclosure.

When the user selects "Add medication," system 130 may generate GUI 700, shown in FIG. 7A. GUI 700 may be configured to display, via drop-down list 702, one or more trial regimens associated with the patient. The user may select a regimen from drop-down list 702 to import medications associated with the selected regimen. The user may then select the "Next" button 704 to continue adding a medication to the patient's EHR.

Concomitant medication module 230 may be configured to receive the selection of a regimen and retrieve, e.g., from a database, one or more drugs associated with the regimen. The one or more drugs may be displayed to the user via GUI 706 shown in FIG. 7B. GUI 706 may be configured to display a table 708 listing the drugs and related information, e.g., information from the patient's EHR.

The user may select one or more drugs from table 708 to add the one or more drugs to the patient's EHR. The selected drug may then be displayed in the patient's EHR as shown in GUI 800 of FIG. 8. Through GUI 800, the user may add further detail to the listed medication 810.

FIGS. 9A-9F illustrate several views of an exemplary GUI 900 for editing a medication. The user may select to add detail to a medication, e.g., medication 810 of GUI 800. Responsive to the request to edit the medication, concomitant medication module 230 may query a formulary database to retrieve formulary data, e.g., formulary data 190, associated with the selected drug. Formulary data may include, for example, commercially available dosages.

GUI 900 may be configured to display the previously selected regimen 902 and the selected medication 904. GUI 900 may further be configured to display input fields associated with the retrieved formulary data. For example, GUI 900 may provide a list 906 of selectable doses, a drop-down list 908 of available formulations, and/or a drop-down list 910 of available routes. GUI 900 may be further configured to receive, from the user via an I/O device of client device 160 (e.g., a touchscreen), input indicative of a start date 912 of the medication and an end date 914 of the medication.

Figure 9A:
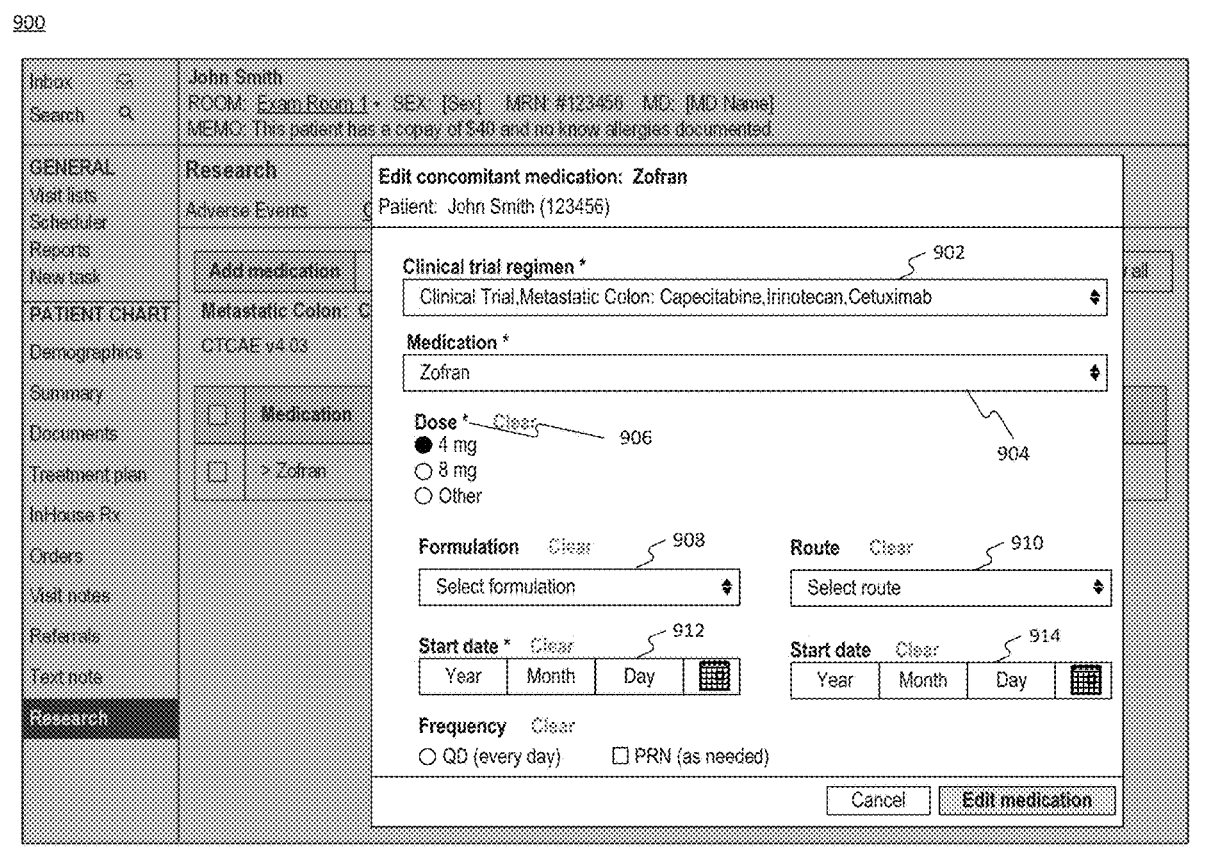
Figure 9B:
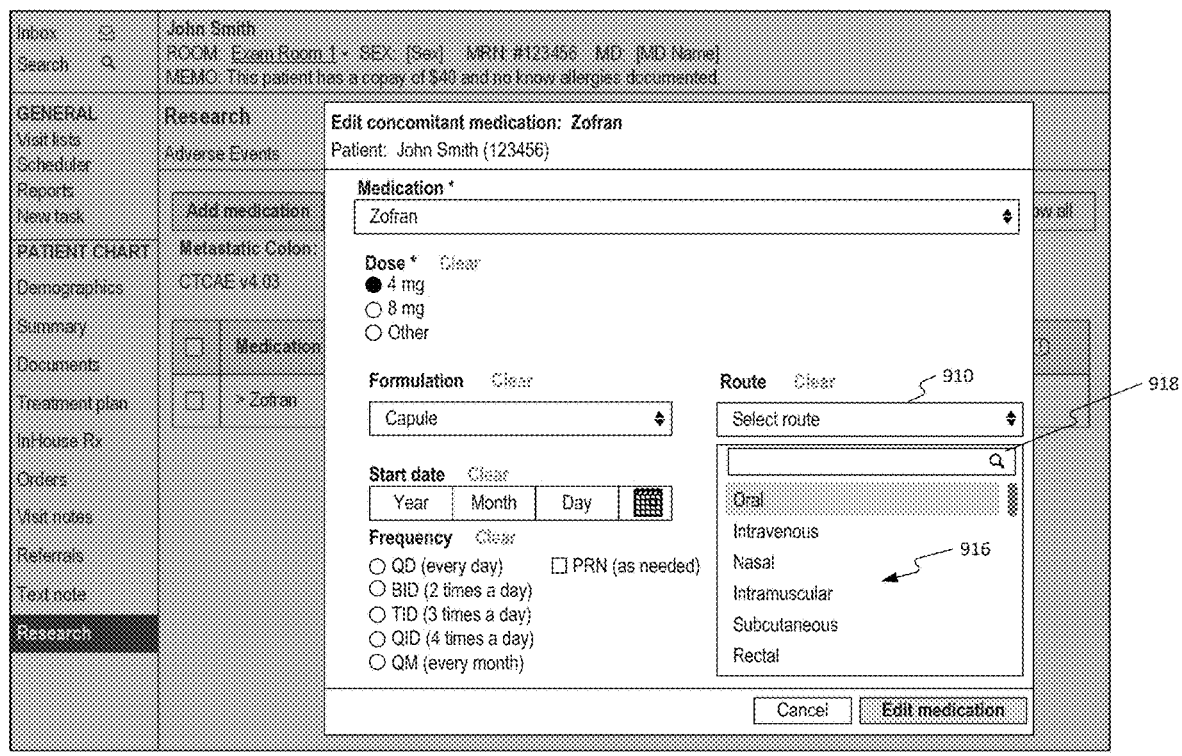

Another view of GUI 900 is shown in FIG. 9B. In FIG. 9B, an expanded drop-down menu 910 is shown. The user may select an option from the list 916, or may enter a search term via text box 918. The search term may be used to search a formulary database to identify records matching the selected drug and the input search term. For example, the user may input a search term to search for a particular route of the selected drug. Similar functionality may be available to enable the user to search for formulations via menu 908. Both menus 908 and 910 may be pre-populated, for example, using data retrieved from the formulary database.

Figure 9C:
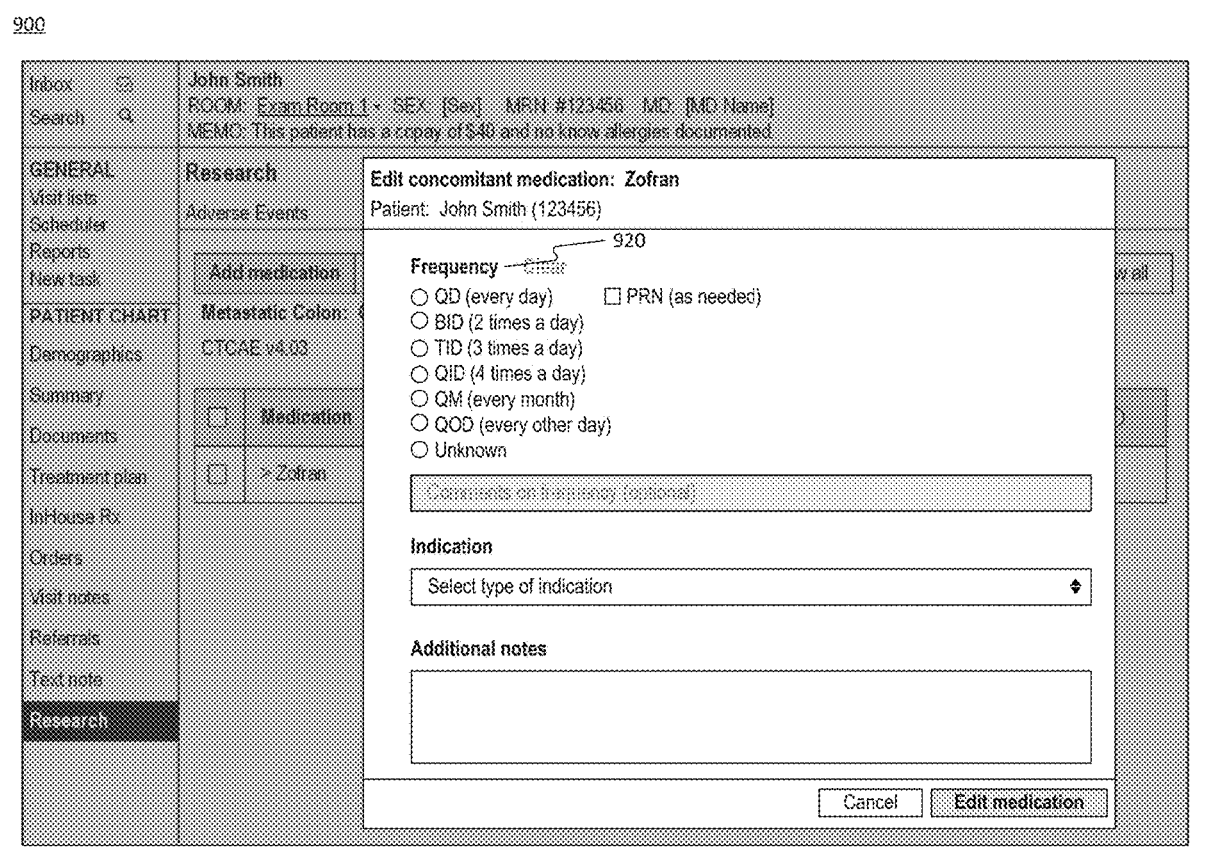

Another view of GUI 900 is shown in FIG. 9C. In FIG. 9C, the user may select, using, e.g., a radio button, a frequency 920 with which the drug is administered to the patient. The descriptions of frequencies may, in some embodiments, be based on frequencies indicated for the selected drug in the formulary database.

Figure 9D:
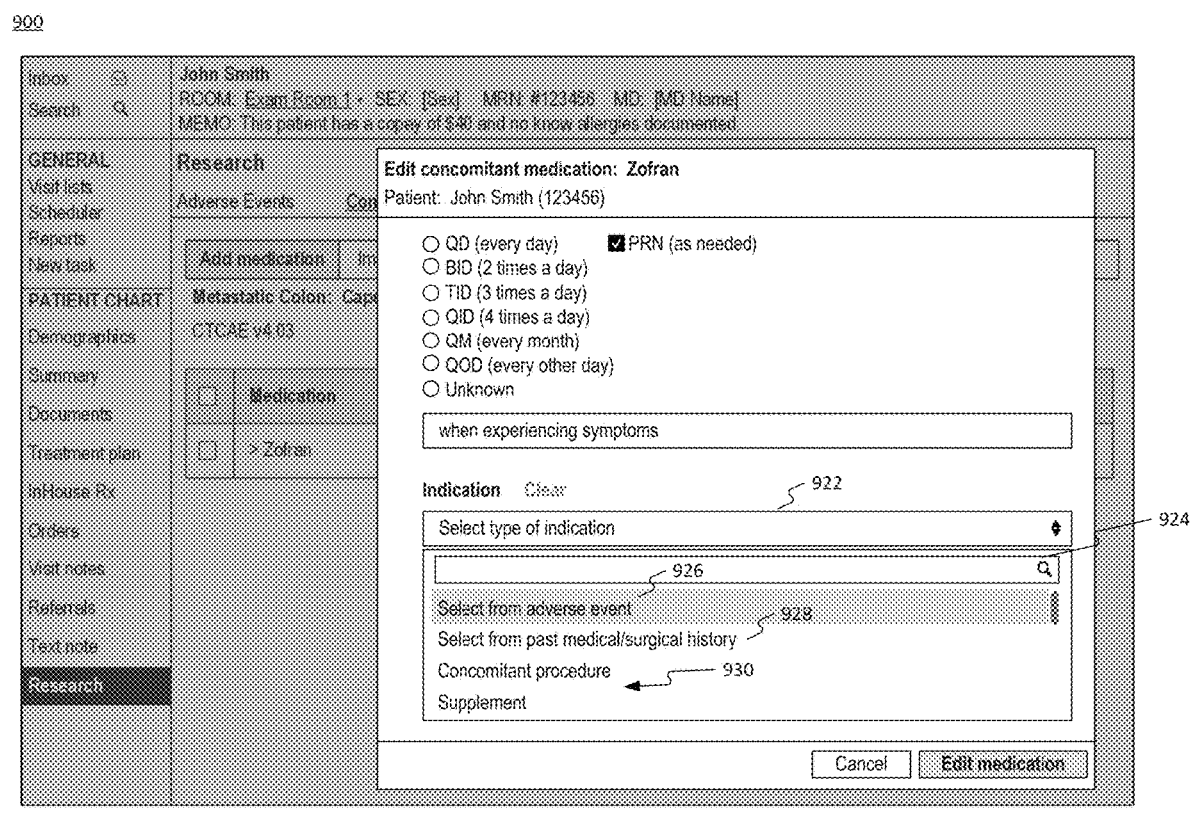

FIG. 9D illustrates a view of GUI 900 through which the user may select a type of indication for the drug. GUI 900 may display a drop-down list 922 including a text box 924, an option to select an adverse event 926, and option to select from past medical history 928, and one or more pre-populated indication types 930. As previously described, the user may enter a search term in text box 924 to search the indication types available (e.g., Select from Conmed, Select from PMH, Supplement, Prophylactic etc.).

Figure 9E:
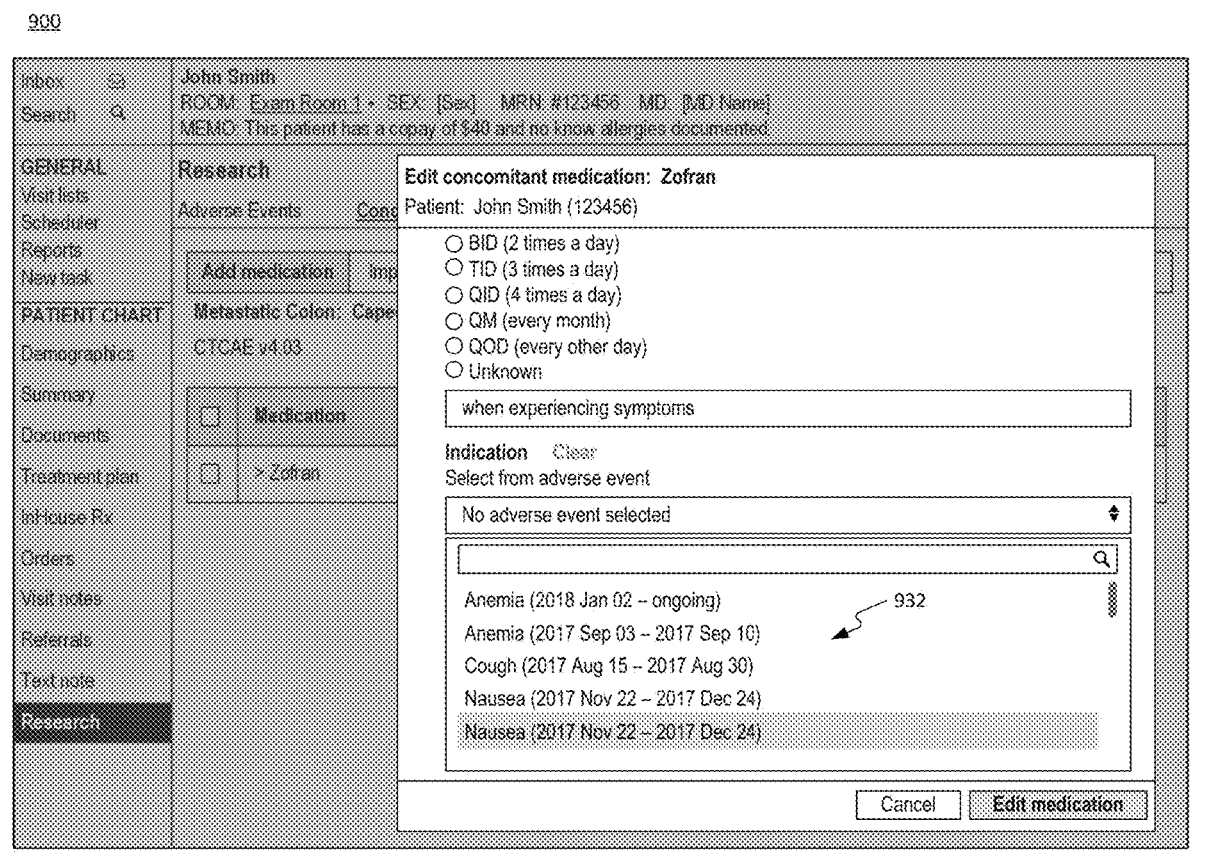

In some embodiments, the user may choose to select an indication from a listing of adverse events recorded for the patient. If the user opts to select from adverse events, GUI 900 may display a listing 932 of adverse events recorded in the patient's EHR, as shown in FIG. 9E. In another embodiment, the user may choose to link the medication to a past medical event. If the user opts to select from past medical events, for example, the GUI may display a listing of past medical events in the patient's EHR, e.g., medical events recorded by the process described with reference to medical history module 240.

Figure 9F:
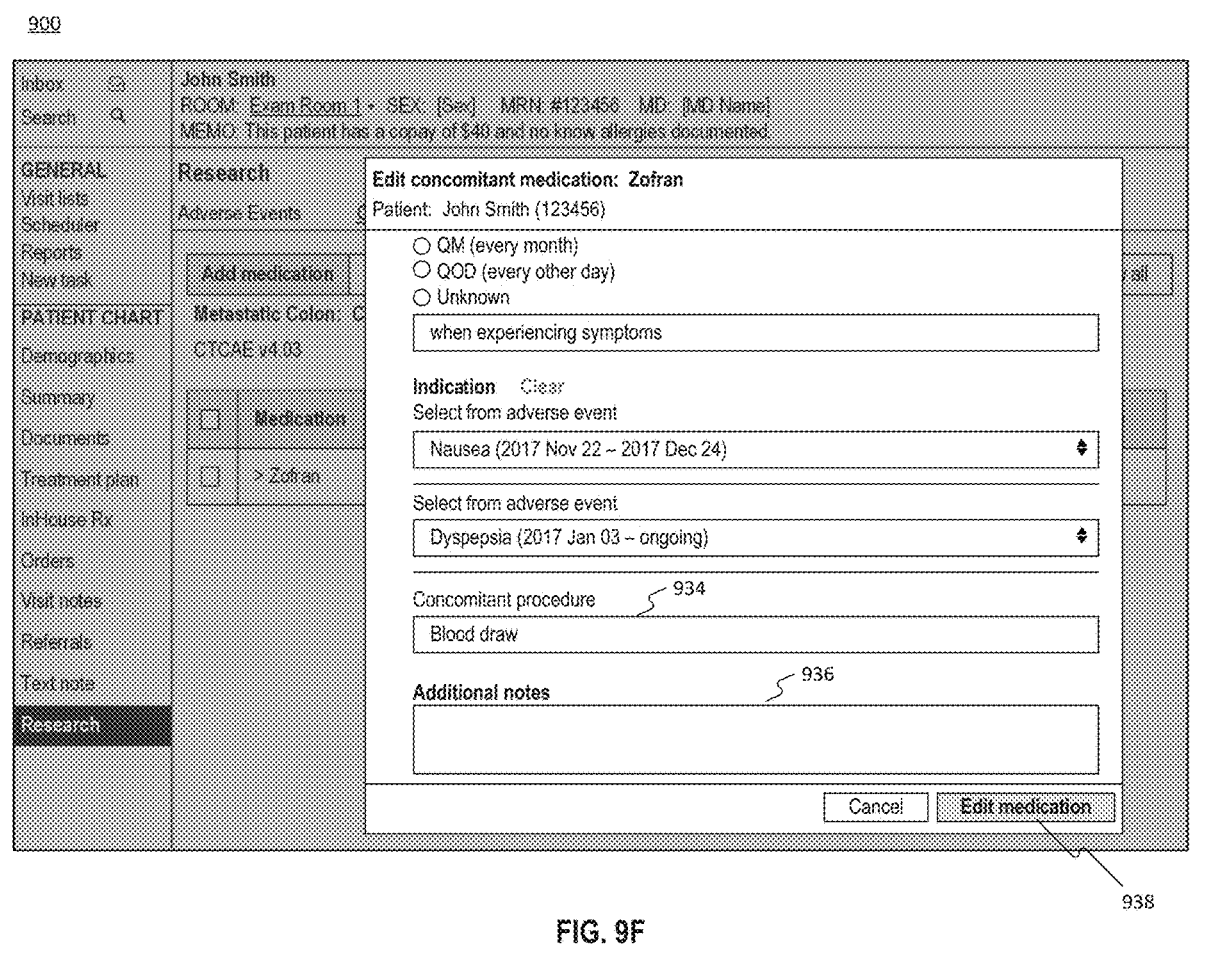

As shown in FIG. 9F, GUI 900 may receive additional information including concomitant procedures 934 or additional notes 936, which may be received as free-text in an input box. A user may then select the "Edit medication" button 938 to save the data input via GUI 900.

FIGS. 10A and 10B are illustrations of views of exemplary GUI 1000 for viewing patient EHR data. In FIG. 10A, GUI 1000 may display the added medication and data related to one or more additional fields. In some embodiments, as shown in FIG. 10B, GUI 1000 may be configured to display modification information 1002, e.g., when the medication was added and by which user and/or when the medication information was edited, and by which user. GUI 1000 may also be configured to display other concomitant medications 1004 associated with the patient EHR.

Figure 11:
FIG. 11 is in illustration of an exemplary GUI consistent with the present disclosure.

FIG. 11 illustrates a GUI 1100 displaying a patient EHR. The user may select the "Add medical history" button 1102 to add a medical or surgical event to the patient's EHR. For example, selecting "Add medical history" may initiate the process described above with reference to medical history module 240.

Figure 12A:

When the user selects "Add medical history," system 130 may generate GUI 1200, shown in FIG. 12A. GUI 1200 may be configured to display, via drop-down list 1202, one or more trial regimens associated with the patient. The user may select a regimen from drop-down list 1202 with which the user wishes to link the medical event.

The user may then enter a search term in text box 1204. System 130 may be configured to query a database, e.g., an adverse event database containing CTCAE data, based on the received search term. In some embodiments, system 130 may retrieve database records containing the search term. As previously described, a GUI may display a list of selectable search results to the user. In other embodiments, text box 1204 may be configured to receive free-text input describing the medical event from the user.

GUI 1200 may also display one or more input fields 1210 configured to receive a selection of a grade, e.g., 1 through 5. If the user selected an event by searching the adverse event database, grades 1 through 5 may be populated with description information associated with the selected event. In other embodiments, the grade may be displayed as the numerical values 1 through 5, for the user to select from.

GUI 1200 may further be configured to receive a start date 1206 and end date 1208 of the medical event. As shown in FIG. 12B, which is another view of GUI 1200, a user may input an indication of an outcome 1212 of the medical event and/or an indication 1214 of whether a concomitant medicine was taken in association with the medical event.

Once the user has input all or some of the above described information, the user may select "Add medical history" button 1216 to add the medical event to the patient EHR. Once the medical event is saved to the patient's EHR, it may be displayed, as shown in GUI 1300 of FIG. 13.

Figure 14:
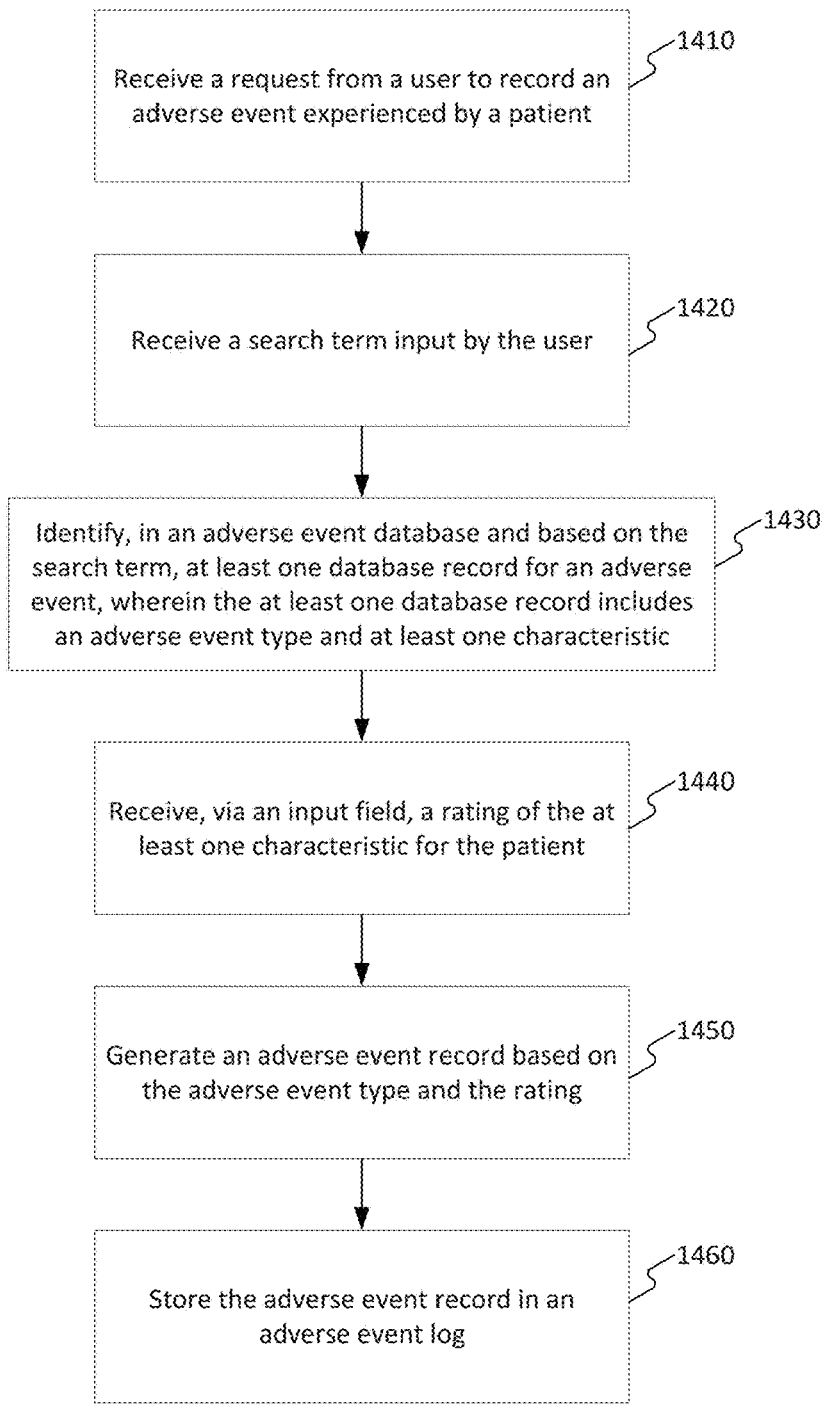
FIG. 14 is a flowchart illustrating an exemplary process for tracking adverse events consistent with the present disclosure.

FIG. 14 illustrates an exemplary process 1400 for tracking adverse events. Process 1400 may be implemented, for example, a processor 140 of system 100, shown in FIG. 1.

At step 1410, the system may receive a request from a user to record an adverse event experienced by a patient. For example, the user may initiate process 1400 via an EHR portal. The request may be generated by client device 160 in response to a command received from the user. The request may then be transmitted to system 130, for example, by network 120.

At step 1420, processor 140 may receive a search term input by the user. For example, a user may input a search term, e.g., via keyboard or touchscreen of client device 160, associated with an adverse event via GUI 400, described with reference to FIG. 4A.

At step 1430, processor 140 may identify, in an adverse event database and based on the search term, at least one database record for an adverse event, wherein the at least one database record includes an adverse event type and at least one characteristic. For example, processor 140 may query an adverse event database storing adverse event data 180 to identify at least one adverse event containing or matching the search term. In some embodiments, the query may identify at least one adverse event containing a partial match of the search term. In some embodiments, processor 140 may identify an adverse event based on whether the regimen name, description, or other associated information contain at least a partial match of the search term. Characteristics associated with an adverse event may include, for example, a grade, an indication of severity, a baseline, and the like.

In some embodiments, processor 140 may display, via a graphical user interface, a selectable identifier associated with each adverse event identified in step 1430. Processor 140 may transmit the search results to client device 160, thereby causing client device 160 to display the GUI. As previously described, processor 140 may determine a relevance score associated with each record based on, for example, a number of times the search term appears in the record. The GUI may be configured to display a ranked list of search results, where the most relevant results are listed first. In another embodiment, the GUI may display a predetermined number of results, e.g., the top 20 results.

At step 1440, processor 140 may receive, via an input field, a rating of the at least one characteristic for the patient. For example, the user may click on an adverse event on a display of client device 160. The selection may be transmitted to processing device 140 via network 120. In some embodiments, processor 140 may be a processor of client device 160. The selection may be received, for example, as a result of the user clicking on the adverse event with a cursor or hovering over the adverse event. In some embodiments, the GUI may include one or more of a radio button, a link, or a checkbox configured to receive a selection from the user.

As described with reference to FIGS. 4B-4D, system 130 may be configured to receive information associated with one or more characteristics of the selected adverse event. For example, via GUI 412, a user may select a grade associated with the adverse event. The grade may be based on, for example, whether a patient has clinical attributes matching those displayed via GUI 412. In some embodiments, the displayed clinical attributes may be retrieved from an adverse event database and may be associated with the selected adverse event.

At step 1450, processor 140 may generate an adverse event record based on the adverse event type and the rating. For example, the generated record may include information such as, the grade of the adverse event experienced by the patient, the seriousness of the event, a start date of the event, an end date of the event, and the like.

At step 1460, processor 140 may store the adverse event record in an adverse event log. In some embodiments, the adverse event log may be a part of EHR database 150. In some embodiments, the adverse event record may include a status. When the record is stored, the status may initially indicate that the record is unsigned. In some embodiments, the user may further associate an adverse event record with a supervisor or other administrator whose signature is required.

Process 1400 may further include steps for receiving sign-off on one or more unsigned adverse event records. For example, processor 140 may generate an alert to a supervisor or person to whom the record was assigned. The alert may be, for example, an email message, pop-up alert, and/or text message and may be transmitted to and displayed by a client device 160 or other device associated with the supervisor.

Processor 140 may be configured to receive a digital signature from the supervisor once the supervisor has reviewed the assigned adverse event record. In some embodiments, the supervisor may not digitally sign the record until the user provides credentials, such as a username and password. Upon receipt of the digital signature, the supervisor may save the adverse event record with an updated status indicating that the record was signed.

Figure 15:
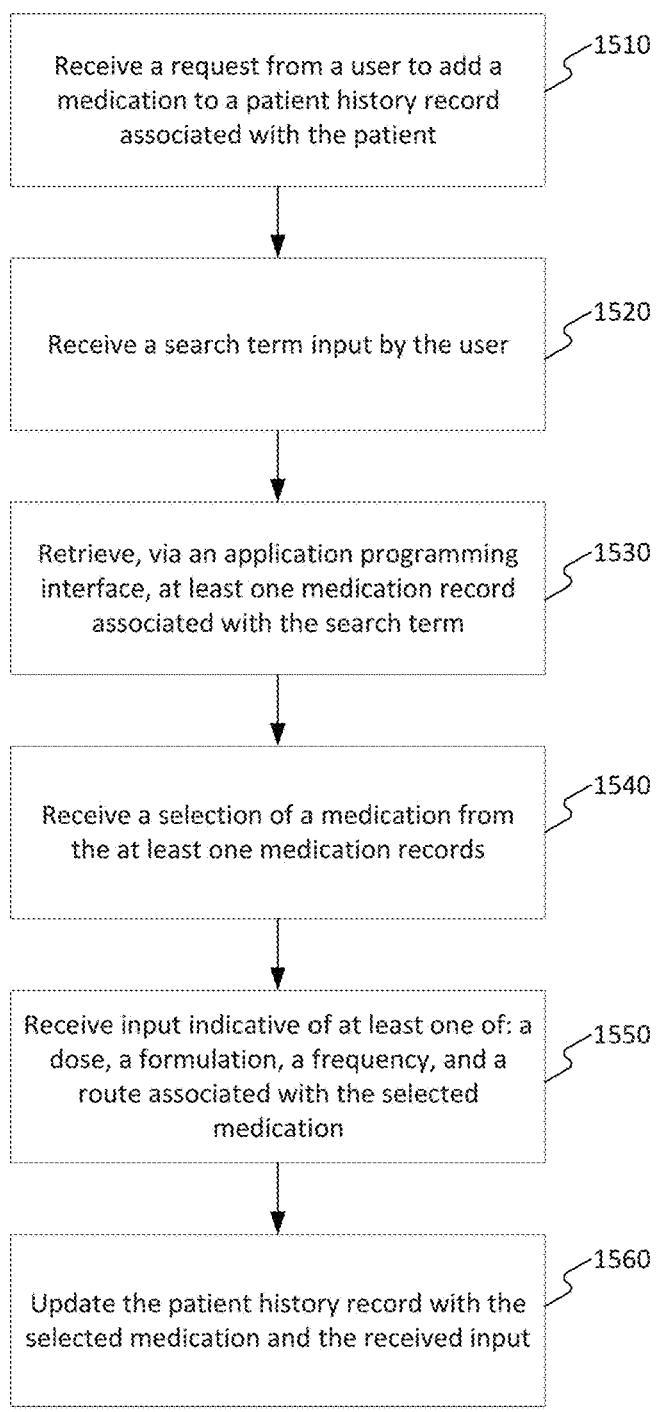
FIG. 15 is a flowchart illustrating an exemplary process for tracking medical information associated with a patient consistent with the present disclosure.

FIG. 15 illustrates an exemplary process 1500 for tracking medical information associated with a patient. Process 1500 may be implemented, for example, a processor 140 of system 100, shown in FIG. 1.

At step 1510, the system may receive a request from a user to add a medication to a patient history record (e.g., patient EHR) associated with the patient. For example, the user may initiate process 1500 via GUI 1100 of an EHR portal. The request may be generated by client device 160 in response to a command received from the user. The request may then be transmitted to system 130, for example, by network 120.

At step 1520, processor 140 may receive a search term input by the user. For example, a user may input a search term associated with a drug, e.g., a drug name. In other embodiments, as described above, the user may import one or more drugs associated with a regimen of the patient.

At step 1530, processor 140 may retrieve, via an application programming interface, at least one medication record associated with the search term. For example, processor 140 may query a formulary database storing formulary data 190 to identify at least one medication containing or matching the search term. In some embodiments, the query may identify at least one medication containing a partial match of the search term. In some embodiments, processor 140 may identify a medication based on whether the medication name, description, or other associated information contain at least a partial match of the search term.

In some embodiments, processor 140 may display, via a graphical user interface, a selectable identifier associated with each medication retrieved in step 1530. Processor 140 may transmit the search results to client device 160, thereby causing client device 160 to display the GUI. As previously described, processor 140 may determine a relevance score associated with each record based on, for example, a number of times the search term appears in the record. The GUI may be configured to display a ranked list of search results, where the most relevant results are listed first. In another embodiment, the GUI may display a predetermined number of results, e.g., the top 20 results.

At step 1540, processor 140 may receive a selection of a medication from the at least one medication records. For example, the user may click on a medication on a display of client device 160. The selection may be transmitted to processing device 140 via network 120. In some embodiments, the GUI may include one or more of a radio button, a link, or a checkbox configured to receive a selection from the user.

As described with reference to FIGS. 9A-9F, system 130 may be configured to receive information associated with medication. For example, GUI 900 may display to the user one or more input fields configured to receive information associated with the particular medication administered to the patient.

At step 1550, processor 140 may receive input indicative of at least one of: a dose, a formulation, a frequency, and a route associated with the selected medication. As described with reference to FIGS. 9A-9F, GUI 900 may display selectable values. For example, system 130 may receive, via an API, information indicating commercially available dosages of the medication. A user may be prompted to select one from a list of the available dosages.

At step 1560, processor 140 may update the patient history record with the selected medication and the received input.

Process 1500 may further include receiving a request to add a medical event to the patient history record. For example, the user may initiate the process for adding a medical event via GUI 1100. System 130 may then, via a GUI, receive a second search term associated with the medical event. In some embodiments, system 130 may identify, in a medical event database, at least one event type associated with the search term. In some embodiments, the medical event database may be the same as an adverse event database storing adverse event data 180.

System 130 may be further configured to receive a selection of an event type, e.g., via GUI 1200. As described above with reference to FIGS. 12A and 12B, via GUI 1200, system 130 may receive information associated with the selected medical event. For example, received information may include a grade (e.g., a level of severity), a start date, an end date, an outcome, an indication, and/or a concomitant procedure. System 130 may then update the patient history record with the event type and the received information.

As described above with reference to process 1400, process 1500 may also include steps for receiving sign-off on one or more unsigned medication and/or medical event records. For example, processor 140 may generate an alert to a supervisor or person to whom the record was assigned. The alert may be, for example, an email message, pop-up alert, and/or text message and may be transmitted to and displayed by a client device 160 or another device associated with the supervisor.

Processor 140 may be configured to receive a digital signature from the supervisor once the supervisor has reviewed the assigned record. In some embodiments, the supervisor may not digitally sign the record until the user provides credentials, such as a username and password. Upon receipt of the digital signature, the supervisor may save the record with an updated status indicating that the record was signed.

The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, 4K Ultra HD Blu-ray, or other optical drive media.

Computer programs based on the written description and disclosed methods are within the skill of an experienced developer. The various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, Python, R, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. A system for tracking adverse events, the system comprising:
    at least one processing device programmed to:
        receive a request from a user to record an adverse event experienced by a patient;
        receive a search term input by the user;
        identify, in an adverse event database and based on the search term, at least one database record for an adverse event, wherein the at least one database record includes an adverse event type and at least one characteristic;
        receive, via an input field, a rating of the at least one characteristic for the patient;
        generate an adverse event record based on the adverse event type and the rating;
        store the adverse event record in an adverse event log;
        based on the storage of the adverse event record, assign the adverse event record an initial record status used for assigning the adverse event record for review; and
        display, on a first graphical user interface, an indication of the initial record status of the adverse event record.

2. The system of claim 1, wherein the request to record the adverse event is received from the user via the first graphical user interface.

3. The system of claim 2, wherein the adverse event is associated with a trial regimen and the at least one processing device is further programmed to:
    receive a measure of relatedness of the adverse event type to the trial regimen.

4. The system of claim 3, wherein the at least one processing device is further programmed to:

receive an indication of the trial regimen via the first graphical user interface.

5. The system of claim 1, wherein the search term is received from the user via a second graphical user interface.

6. The system of claim 1, wherein the search term is associated with the adverse event experienced by the patient.

7. The system of claim 1, wherein identifying the at least one database record in the adverse event database comprises:
generating a relevance score for each database record in the adverse event database based on a comparison of each database record to the search term;
ranking the database records based on the relevance score; and
displaying, to the user, a predetermined number of the ranked database records.

8. The system of claim 1, wherein the identified at least one database record comprises the search term.

9. The system of claim 1, wherein the identified at least one database record comprises at least a portion of the search term.

10. The system of claim 1, wherein the rating of the at least one characteristic for the patient is received via a second graphical user interface.

11. The system of claim 1, wherein the rating comprises a level of severity of the adverse event experienced by the patient.

12. The system of claim 1, wherein based on an update to the initial record status of the adverse event record, the at least one processing device is further programmed to update the displayed indication of the initial record status of the adverse event record to indicate an updated record status.

13. The system of claim 12, wherein the displayed indication of the initial record status of the adverse event record comprises an indication of an unsigned record status.

14. The system of claim 13, wherein the at least one processing device is further programmed to:
transmit, after storing the adverse event record in the adverse event log, an alert to a device associated with a supervising physician;
receive, from the device associated with the supervising physician, a digital signature associated with the adverse event record; and
update the displayed indication of the initial record status of the adverse event record to an indication of a signed record status.

15. The system of claim 14, wherein the at least one processing device is further programmed to:
authenticate the supervising physician prior to receiving the digital signature.

16. A method for tracking adverse events, the method comprising:
receiving a request from a user to record an adverse event experienced by a patient;
receiving a search term input by the user;
identifying, in an adverse event database and based on the search term, at least one database record for an adverse event, wherein the at least one database record includes an adverse event type and at least one characteristic;
receiving, via an input field, a rating of the at least one characteristic for the patient;
generating an adverse event record based on the adverse event type and the rating;
storing the adverse event record in an adverse event log;
based on the storage of the adverse event record, assigning the adverse event record an initial record status used for assigning the adverse event record for review; and
displaying, on a first graphical user interface, an indication of the initial record status of the adverse event record.

17. The method of claim 16, wherein the request to record the adverse event is received from the user via the first graphical user interface.

18. The method of claim 17, wherein the adverse event is associated with a trial regimen and the method further comprises:
receiving a measure of relatedness of the adverse event type to the trial regimen.

19. The method of claim 18, wherein the method further comprises:
receiving an indication of the trial regimen via the first graphical user interface.

20. The method of claim 16, wherein the search term is received from the user via a second graphical user interface.

21. The method of claim 16, wherein the search term is associated with the adverse event experienced by the patient.

22. The method of claim 16, wherein identifying the at least one database record in the adverse event database comprises:
generating a relevance score for each database record in the adverse event database based on a comparison of each database record to the search term;
ranking the database records based on the relevance score; and
displaying, to the user, a predetermined number of the ranked database records.

23. The method of claim 16, wherein the identified at least one database record comprises the search term.

24. The method of claim 16, wherein the identified at least one database record comprises at least a portion of the search term.

25. The method of claim 16, wherein the rating of the at least one characteristic for the patient is received via a second graphical user interface.

26. The method of claim 16, wherein the rating comprises a level of severity of the adverse event experienced by the patient.

27. The method of claim 16, further comprising, based on an update to the initial record status of the adverse event record, updating the displayed indication of the initial record status of the adverse event record to indicate an updated record status.

28. The method of claim 27, wherein the displayed indication of the initial record status of the adverse event record comprises an indication of an unsigned record status.

29. The method of claim 28, further comprising:
transmitting, after storing the adverse event record in the adverse event log, an alert to a device associated with a supervising physician;
receiving, from the device associated with the supervising physician, a digital signature associated with the adverse event record; and
updating the displayed indication of the initial record status of the adverse event record to an indication of a signed record status.

30. The system of claim 29, further comprising:
authenticating the supervising physician prior to receiving the digital signature.

31. A computer-readable medium storing instructions that when executed cause a processing device to:

receive a request from a user to record an adverse event experienced by a patient;
receive a search term input by the user;
identify, in an adverse event database and based on the search term, at least one database record for an adverse event, wherein the at least one database record includes an adverse event type and at least one characteristic;
receive, via an input field, a rating of the at least one characteristic for the patient;
generate an adverse event record based on the adverse event type and the rating;
store the adverse event record in an adverse event log;
based on the storage of the adverse event record, assign the adverse event record an initial record status used for assigning the adverse event record for review; and
display, on a first graphical user interface, an indication of the initial record status of the adverse event record.

* * * * *